(12) United States Patent
Muller et al.

(10) Patent No.: US 8,213,016 B2
(45) Date of Patent: Jul. 3, 2012

(54) TURBIDITY MEASURING DEVICE AND A METHOD FOR DETERMING A CONCENTRATION OF A TURBIDITY-CAUSING MATERIAL

(75) Inventors: Andreas Muller, Ostfildern (DE); Rudiger Frank, Haigerloch (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 100 days.

(21) Appl. No.: 12/805,071

(22) Filed: Jul. 12, 2010

(65) Prior Publication Data

US 2011/0019194 A1 Jan. 27, 2011

(30) Foreign Application Priority Data

Jul. 22, 2009 (DE) .......................... 10 2009 027 929

(51) Int. Cl.
*G01N 21/00* (2006.01)

(52) U.S. Cl. ........................................ 356/442; 356/432

(58) Field of Classification Search .......... 356/432–435, 356/440–442
See application file for complete search history.

(56) References Cited

FOREIGN PATENT DOCUMENTS

| DE | 41 42 938 C2 | 4/1995 |
|----|--------------|--------|
| DE | 10 2008 010 446 A1 | 9/2009 |
| FR | 10 2008 018 592 A1 | 10/2009 |

*Primary Examiner* — Tri T Ton
(74) *Attorney, Agent, or Firm* — Bacon & Thomas, PLLC

(57) ABSTRACT

A turbidity measuring device having a four-beam, alternating light arrangement for registering turbidity of a measured medium includes first and second light sources $L_1$, $L_2$; and first and second receivers $R_1$, $R_2$. The direct measuring paths extend from light sources $L_i$, through a measured medium, to receivers $R_i$, and indirect measuring paths extend from light sources $L_i$, through the measured medium, to second receivers $R_j$; wherein $i \neq j$; wherein turbidity can be ascertained as a function of a quotient A/B by means of an evaluating circuit; wherein A and B are functions at least of signals registered via the direct or indirect measuring paths; wherein at least a first monitor signal, which depends on the first light source, enters into one of the two terms A or B; wherein the light reaches the monitor from the first light source without interaction with the measured medium; and wherein the monitor signal is added to at least one of the signals registered via the measuring paths and entering into the term A or B.

10 Claims, 3 Drawing Sheets

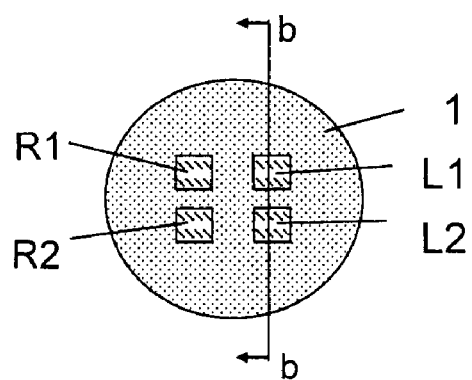
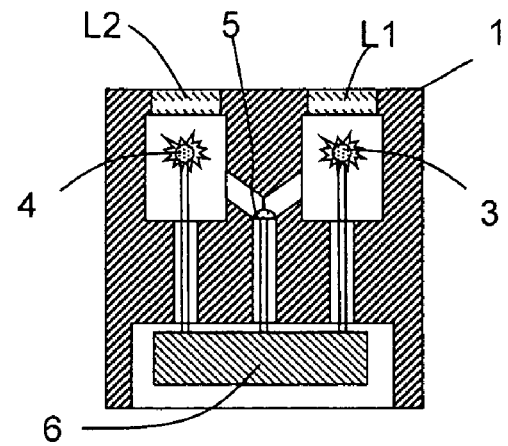
Fig. 1a
Fig. 1b
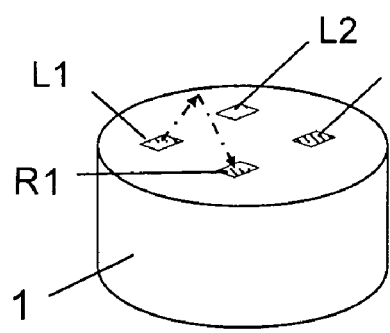
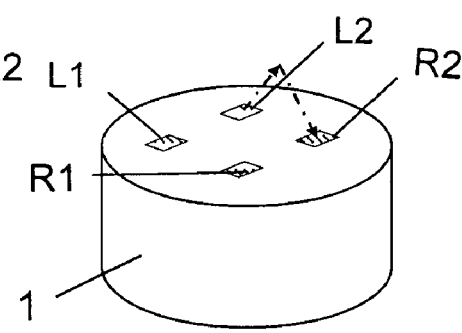
Fig. 2a
Fig. 2b
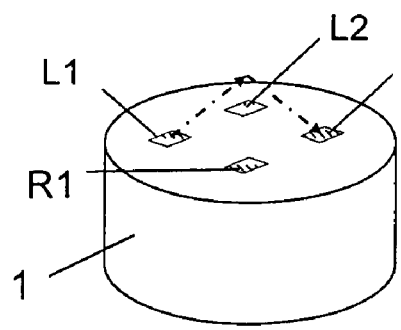
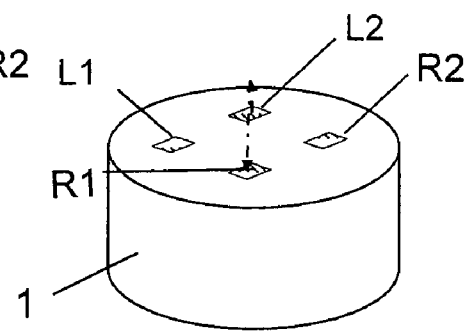
Fig. 2c
Fig. 2d

TURBIDITY MEASURING DEVICE AND A METHOD FOR DETERMING A CONCENTRATION OF A TURBIDITY-CAUSING MATERIAL

TECHNICAL FIELD

The present invention relates to a turbidity measuring device and a method for determining a concentration of a turbidity-causing material in a medium, especially a turbidity measuring device according to the four-beam, alternating light principle, and a method using the four-beam, alternating light principle.

BACKGROUND DISCUSSION

A turbidity measuring device according to the four-beam, alternating light principle includes at least two light sources and at least two receivers, wherein four measuring paths are defined between the two measuring sources and the two receivers, via which the light emitted by the light sources reaches the receivers; wherein, on at least two measuring paths, the light reaches the receiver through scattering. In general, the signal $S_{ij}$ (T) of the receiver $R_j$, which receives light emitted by the light source $L_i$ following an interaction with a measured medium, is given by Equation 1.

$$S_{ij}(T) = I_i \cdot c_{ij} \cdot T \cdot e^{-\frac{T \cdot X_{ij}}{\lambda}} \qquad (1)$$

In such a case, $I_i$ is the intensity of the emitted light; $C_{ij}$ a is constant, which is dependent on the geometrical boundary conditions of the turbidity measuring device and the scattering properties of the turbidity-causing material, $X_{ij}$ is the measuring path length in the measured medium between the light source $L_i$ and the receiver $R_j$, and $\lambda$ is a coefficient, which describes the scattering and absorption characteristics of the turbidity-causing material with regard to the radiated light, wherein the turbidity-causing material is present in a concentration T.

In order to eliminate the influence of variable device parameters such as, for example, the intensity of the radiated light $I_1$, $I_2$ and transmission characteristics of windows, the measured variable FAL(T)—defined in Equation 2—is introduced (the acronym FAL comes from Four-beam, Alternating Light), the explicit representation of which is given in Equation 3.

$$FAL(T) = \frac{S_{11}(T) \cdot S_{22}(T)}{S_{12}(T) \cdot S_{21}(T)} \qquad (2)$$

$$FAL(T) = \frac{c_{11} \cdot c_{22}}{c_{12} \cdot c_{21}} \cdot e^{T \frac{X_{12}+X_{21}-X_{11}-X_{22}}{\lambda}} \qquad (3)$$

It should be recognized here, that the measured variable FAL(T) is independent of the radiated intensities, and the dependence of the concentration T on the turbidity-causing material is present only in the exponential function.

If one furthermore assumes a symmetry in the construction of the turbidity measuring device, this thus meaning that $c_{11}=c_{22}$ and $c_{12}=c_{21}$, as well as $X_{11}=X_{22}=X_{direct}$ and $X_{12}=X_{21}=X_{indirect}$, then the measured variable FAL(T) can be represented in the form of Equation 4:

$$FAL(T) = c \cdot e^{2 \cdot T \frac{X_{indirect}-X_{direct}}{\lambda}}, \qquad (4)$$

wherein c represents the quotient of the coefficients.

In FIG. 4a, an example of a curve of an FAL-signal, represented as a function of the content T of the turbidity-causing material (TCM), is presented as solid line. For high concentrations of turbidity-causing material, the FAL-signal is a good signal to evaluate, and directly enables an association between signal value and content of turbidity-causing material. In the case of low concentrations, below the maximum of the signal of the individual measurement channels $S_{ij}$, the FAL-signal has, however, weaknesses, which make an exact determining of the concentration of turbidity-causing material difficult, because (as is presented in Equation 5), for low concentrations, the variable FAL(T) converges toward the constant C, so that a dependence on the concentration of turbidity-causing material is practically no longer given.

$$FAL(T) \xrightarrow{T<<\frac{\lambda}{\Delta X}} c \cdot \left(1 + 2 \cdot T \frac{\Delta X}{\lambda}\right) \rightarrow c \qquad (5)$$

(In such a case, $\Delta X := X_{direct} - X_{indirect}$)

The independence of the FAL-signal from the measured variable is again made clear in FIG. 4b, where it is logarithmically plotted versus small values for the content of turbidity-causing material.

SUMMARY OF THE INVENTION

Therefore, an object of the present invention is to provide a turbidity measuring device which overcomes the described disadvantages of the state of the art, and which especially makes possible determining the content of turbidity-causing material in the case of low concentrations thereof. The object is achieved in the invention by the turbidity measuring device which has a four-beam, alternating light arrangement for registering the turbidity of a measured medium, comprises a first light source $L_1$ and a second light source $L_2$, a first receiver $R_1$ and a second receiver $R_2$; wherein a first direct measuring path extends from the first light source $L_1$, through a measured medium, to the first receiver $R_1$; wherein a second direct measuring path extends from the second light source $L_2$ to the second receiver $R_2$; wherein a first indirect measuring path extends from the light source $L_1$, through the measured medium, to the second receiver $R_2$; wherein a second indirect measuring path extends from the second light source $L_2$, through the measured medium, to the first receiver $R_1$; wherein the turbidity can be ascertained as function of a quotient A/B; wherein one of the terms A or B is a function at least of the signals registered via the direct measuring paths; and wherein the other respective term is a function at least of the signals registered via the indirect measuring paths; characterized in that, at least a first monitor signal, which is dependent on the intensity of the first light source, enters into one of the two terms A or B; wherein the light of the first light source reaches the monitor without interaction with the measured medium; and wherein the monitor signal is added to at least one of the signals registered via the measuring paths and entering into the term A or B.

In a further development of the four-beam, alternating light arrangement of the invention, the first monitor signal $I_1 \cdot m$ and a second monitor signal $I_2 \cdot m$ enter into the one of the two terms A or B, wherein the second monitor signal is dependent on the intensity of the second light source, and wherein the light of the second light source reaches a monitor receiver without interaction with the measured medium, and wherein the second monitor signal is added to the other signal ascertained via one of the measuring paths that enters into the term A or B.

The monitor receiver, which provides the second monitor signal, can be the same monitor receiver that provides the first monitor signal, or it can be another monitor receiver.

In a further development of the four-beam, alternating light-arrangement of the invention, the turbidity can be ascertained as a function of a measured variable, which is either defined as FALMN(T) or as FALMD(T), wherein:

$$FALMN(T) = \frac{(S_{11}(T) + I_1 \cdot m) \cdot (S_{22}(T) + I_2 \cdot m)}{S_{12}(T) S_{21}(T)} \quad (6)$$

and $$FALMD(T) = \frac{S_{11}(T) \cdot S_{22}(T)}{(S_{12}(T) + I_1 \cdot m) \cdot (S_{21}(T) + I_2 \cdot m)}. \quad (7)$$

$S_{ij}(T)$ in each case gives the measured light intensity of the light, which following an interaction with the measured medium, arrives from a light source $L_i$ to a receiver $R_j$. $S_{ij}(T)$ is given for modeling by equation (1). The N and D in FALMN(T) and FALMD(T), respectively, indicate numerator and denominator, respectively.

The effect of this formulation for small turbidities is presented in the following for FALMN. The four beam, alternating light signal with a monitor signal in the numerator FALMN(T) can be broken up into the usual four-beam, alternating light signal according to the state of the art and a monitor component. Thus:

$$FALMN(T) = FAL(T) + \quad (8)$$

$$\frac{m}{T} \cdot \frac{\left(c_{11} \cdot e^{\frac{-T \cdot X_{11}}{\lambda}} + c_{22} \cdot e^{\frac{-T \cdot X_{22}}{\lambda}}\right)}{c_{12} \cdot c_{21} \cdot e^{\frac{-T \cdot (X_{12} + X_{21})}{\lambda}}} + \frac{m^2}{T^2} \cdot \frac{1}{c_{12} \cdot c_{21} \cdot e^{\frac{-T \cdot (X_{12} + X_{21})}{\lambda}}}$$

With the assumption of symmetry $c_{direct} := c_{11} = c_{22}$; $c_{indirect} := c_{12} = c_{21}$; $X_{direct} := X_{11} = X_{22}$; and $X_{indirect} := X_{12} = X_{21}$, it follows therefrom that:

$$FALMN(T) = \quad (9)$$

$$FAL(T) + \frac{1}{T} \cdot \frac{2 \cdot m \cdot c_{direct} \cdot e^{\frac{-T \cdot X_{direct}}{\lambda}}}{\left(c_{indirect} \cdot e^{\frac{-T \cdot X_{indirect}}{\lambda}}\right)^2} + \frac{1}{T^2} \frac{m^2}{\left(c_{indirect} \cdot e^{\frac{-T \cdot X_{indirect}}{\lambda}}\right)^2}.$$

For small T, is it also true that:

$$FALMN(T) \xrightarrow{T \to 0} c + \frac{1}{T} \cdot \frac{2 \cdot m \cdot c_{direct}}{(c_{indirect})^2} + \frac{1}{T^2} \frac{m^2}{(c_{indirect})^2}. \quad (10)$$

Thus, the signal for small T has, in the limit value, a proportionality to $(1/T)^2$; it is no longer a constant, and, consequently, an association of the measurement signal with a concentration of turbidity-causing material is made possible.

Corresponding results follow from considerations for FALMD(T).

The resulting data for FALMN(T) and FALMD(T) are presented in FIGS. 3a and 3b.

The assumption of symmetry is not strictly essential to the invention; it serves only to simplify the presentation. In principle, the above considerations are also valid for arrangements in which deviations from symmetry occur.

The compromise, which must be faced when taking into consideration a monitor signal, exists in the fact that the measurement signal FALMN(T) or FALMD(T) does not enable a unique association with a concentration of turbidity-causing material, as is evident from the curves in FIGS. 3a and 3b. In order nevertheless to enable a unique association with a measured value, according to a further development of the invention, the arrangement features an evaluation mode, in which a concentration of turbidity-causing material T(FAL) is ascertained, and a second evaluation mode, in which a concentration of turbidity-causing material T(FALMN) and/or T(FALMD) is ascertained; wherein the second evaluation mode is taken into consideration especially when T(FAL) falls beneath a limit value, for example, $T < \lambda / X_{indirect}$.

A further degree of freedom with regard to the design of the measuring arrangement is clearly provided by the weighting of the monitor expression $I_i \cdot m$ in proportion to the $S_{ij}$ in FALMD or FALMN. In one embodiment, it is provided, for example, that $0.1 < m/c_{ii} < 10$, preferably that $0.2 < m/c_{ii} < 5$, and still more preferably that $0.4 < m/c_{ii} < 2.5$.

To the extent that in the explanation the invention, mathematical operations with signals—thus, for example, multiplication, addition and division of signals—are being discussed here, among those included are, for example, application of the respective mathematical operation to any representation of the signals, and thus especially to digital representations of the respective signal values or analog representations of the respective signal values. The addition of a signal can, according to the invention, also include a weighted addition of the signal, in the case of which the signal is to be multiplied by a weighting factor before the addition. Considerations for a weighting are explained, for example, in the previous paragraph.

BRIEF DESCRIPTION OF THE DRAWINGS

The invention will now be explained on the basis of the example of an embodiment illustrated in the drawing, the figures of which show as follows:

FIG. 1a is a plan view of the end of a probe head of a turbidity measuring device of the invention;

FIG. 1b is a longitudinal section of the probe head of FIG. 1a along the line b-b;

FIGS. 2a to 2d: are representations of the beam paths for ascertaining the signal intensities of the different individual channels;

DETAILED DISCUSSION IN CONJUNCTION WITH THE DRAWINGS

The probe head of a turbidity measuring device shown in FIG. 1a includes an essentially cylindrical, metal housing made of stainless steel, in the end of which four windows are arranged (the corners of which define a rectangle), which seal off a first light source $L_1$ and a second light source $L_2$, a first receiver $R_1$ and a second receiver $R_2$ from the environment surrounding the probe head; wherein the radiation of the first light source $L_1$ and the second light source $L_2$ can pass in and out through the windows.

As is shown in FIG. 1b, the light sources $L_1$ and $L_2$ comprise a first flash lamp 3 and a second flash lamp 4, wherein a monitor diode 5 is arranged between the flash lamps, which registers intensity of the light of the first and second flash lamps, respectively.

The first flash lamp 3, the second flash lamp 4 and the monitor diode 5—as well as the photodiodes (not shown here) of the first receiver $R_1$ and the second receiver $R_2$—are connected to an electronic circuit 6, which controls the flash lamps and selectively registers the signals of the monitor diode 5, as well as those of the photodiodes of the first and second receivers.

FIGS. 2a through 2d show the beam paths through a measured medium, as used for registering the signal intensities for the individual channels of the four-beam, alternating light measurements. FIG. 2a shows the first direct measuring path, in the case of which the first light source $L_1$ and the first receiver $R_1$ are active; this means that the circuit 6 fires the first flash lamp 3 for its emission of light, and registers the signal intensity of the photodiode of the first receiver $R_1$. FIG. 2b shows the second direct measuring path, in the case of which light from the second light source $L_2$ reaches the second receiver $R_2$ through scattering in the medium. Accordingly, the second flash lamp $L_2$ is triggered by the circuit 6 to emit light, wherein the circuit 6 registers the signal of the photodiode of the second receiver $R_2$.

Figure 3:
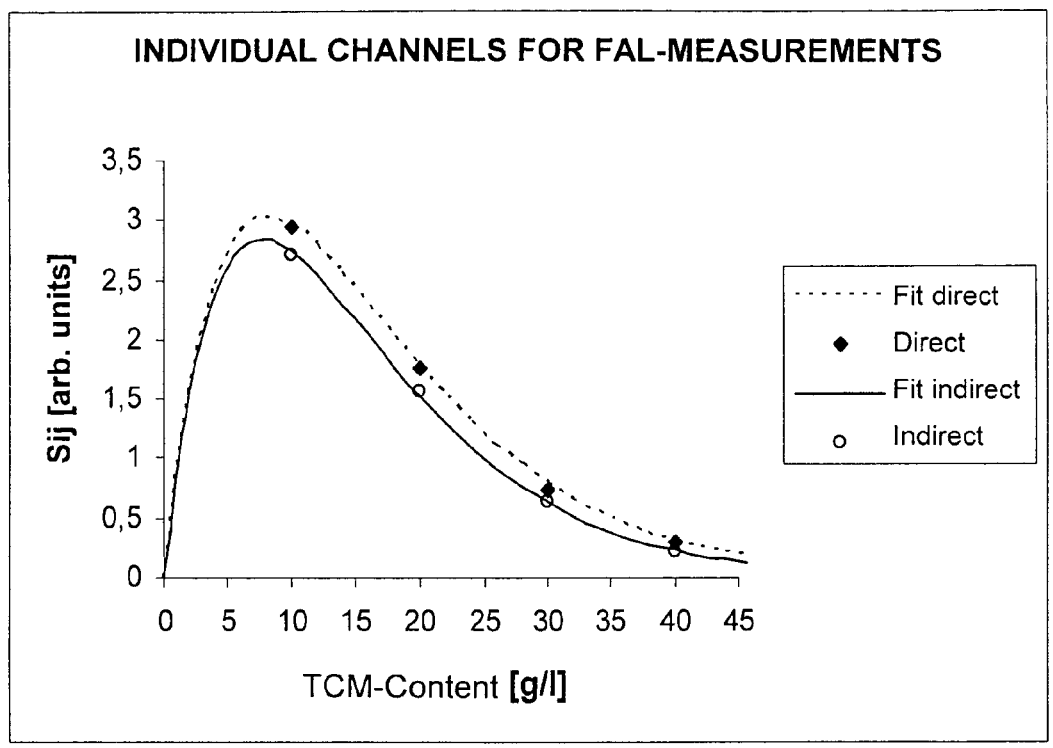
FIG. 3 shows measurement data and fits for the signal intensities of the individual channels.

FIGS. 2c and 2d show the two indirect measuring paths, in the case of which light from the first light source reaches the second receiver, or light from the second light source reaches the first receiver. In FIG. 3, examples of the resulting signals of the individual channels are presented, which for low turbidity-causing material contents run proportional to the turbidity-causing material content, and which for larger values for turbidity-causing material content can be described by an exponential function. The resulting four-beam, alternating light-signal—which is formed from a product of the intensities of the direct measuring paths divided by a product of the intensities of the indirect measuring paths—is represented as a solid line FAL in FIGS. 4a and 4b. As initially explained, for sufficiently high turbidity-causing material contents (for example, in the case of a content of more than 3 grams per liter), the FAL signal provides a usable relationship between the FAL-signal and the content of turbidity-causing material, and thereby enables a sufficiently exact determining of the content of turbidity-causing material. As initially discussed, evaluation of the FAL-signal is no longer useful for low turbidity-causing material contents (say, for example, less than 3 grams per liter) because in this range, the FAL signal is almost constant. Here is where the monitor-aided, four-beam, alternating light of the invention comes into play; either as FALMN, wherein, in this case, the intensity of the associated monitor signal is added to the signal intensities of the individual channels in the numerator; or as FALMD, wherein the intensity of the associated monitor signal is added to the signal intensities of the individual channels in the denominator; wherein the associated monitor signal directly (i.e. without any interaction with the measured medium) registers the intensity of the light emitted by the first or the second flash lamp, and, does so at that point in time, in which is also registered the signal intensity of the individual channel, to which the signal of the monitor diode is to be added.

To the extent that, in the case of the example of an embodiment for determining the four-beam alternating light signal, the product of the signals of the direct measurement channels is in the numerator, and the product of the signals of the indirect measurement channels is in the denominator; for determining the monitor-aided four beam alternating light signal FALMN, the signal of the monitor diode 5 is, in accordance therewith, to be registered in the case of ascertaining the signal intensities of the two direct measuring paths (compare FIGS. 2a and 2b), and to be used, according to Equation 6, for the evaluation.

To the extent that monitor-aided, four-beam, alternating light is to be used with the monitor component in the denominator (FALMD), the signal of the monitor diode 5 is to be registered in the case of ascertaining the signal intensity of the indirect measuring paths (compare FIGS. 2c and 2d) and to be used according to Equation 7.

Figure 4A:
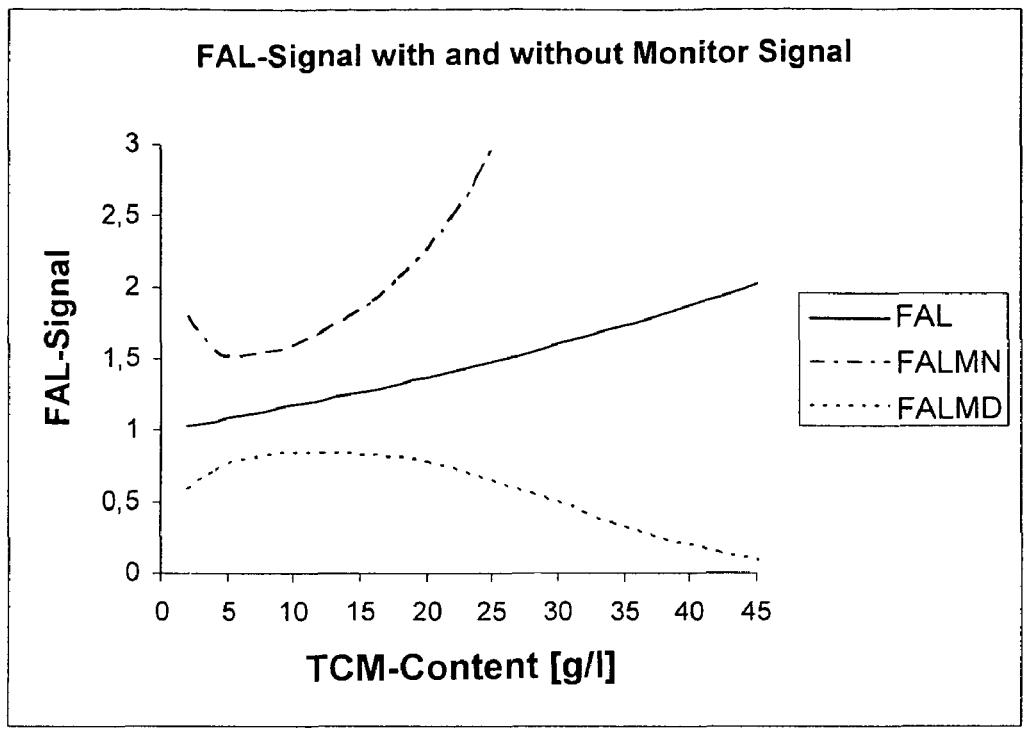
FIG. 4a shows a comparison of a four-beam, alternating light signal as a function of the content of turbidity-causing material according to the state of the art with the corresponding functions of a monitor-aided, four-beam, alternating light-signal according to the present invention.
Figure 4B:
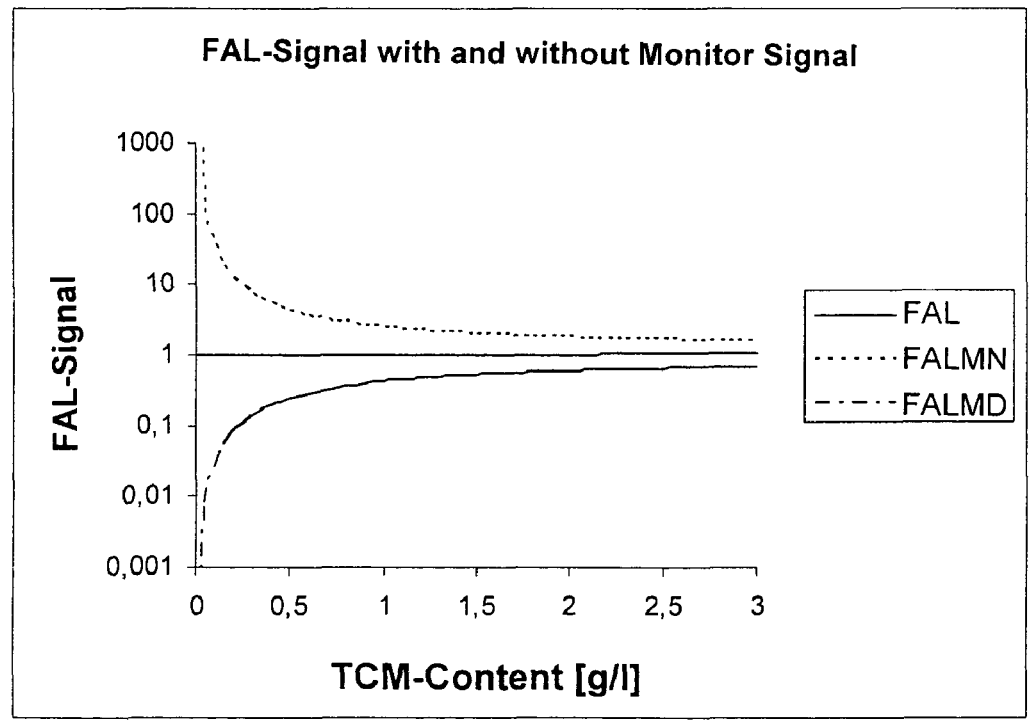
FIG. 4b is a logarithmic presentation of the comparison of a four-beam, alternating light-signal according to the state of the art with a monitor-aided, four-beam, alternating light-signal according to the present invention, for low turbidity-causing material contents.

As is presented in FIGS. 4a and 4b, for low turbidity-causing material contents, both FALMD as well as FALMN deliver a sufficiently dynamic and monotonic relationship between the signal and the turbidity-causing material content. For large contents of turbidity-causing material, it is therefore advantageous to first work with the conventional FAL-signal for determining the turbidity-causing material content, and in the case of small turbidity-causing material contents, to use one monitor-aided four-beam alternating light signal or both monitor-aided four-beam alternating light signals, thus FALMD and/or FALMN.

The invention claimed is:

1. A turbidity measuring device with a four-beam, alternating light arrangement for registering the turbidity of a measured medium, comprising:
  a first light source $L_1$ and a second light source $L_2$; and
  a first receiver $R_1$ and a second receiver $R_2$, wherein:
  a first direct measuring path extends from said first light source $L_1$, through a measured medium, to said first receiver $R_1$;
  a second direct measuring path extends from said second light source $L_2$ to said second receiver $R_2$;
  a first indirect measuring path extends from said light source $L_1$, through the measured medium, to said second receiver $R_2$;
  a second indirect measuring path extends from said second light source $L_2$, through the measured medium, to said first receiver $R_1$;
  the turbidity measuring device has an evaluation circuit, with which turbidity can be ascertained as a function of a quotient A/B;
  one of the terms A or B is a function at least of the signals registered via the direct measuring paths;
  the respectively other term is a function at least of the signals registered via the indirect measuring paths; and
  at least a first monitor signal, which is dependent on the intensity of the first light source, enters into one of the two terms A or B; wherein light from the first light source reaches the monitor without interaction with the measured medium; and the monitor signal is added to at least one of the signals registered via the measuring path and entering into the term A or B.

2. The turbidity measuring device as claimed in claim 1, wherein:
the first monitor signal $I_1 \cdot m$ and a second monitor signal $I_2 \cdot m$ enter into the one of the two terms A or B;
the second monitor signal depends upon the intensity of the second light source;
the light of the second light source reaches a monitor receiver without interaction with the measured medium; and
the second monitor signal is added to the other signal ascertained via one of the measuring paths and entering into the term A or B.

3. The turbidity measuring device as claimed in claim 1, wherein:
the turbidity can be ascertained as a function of a measured variable, which is either defined as FALMN(T) or as FALMD(T), where:

$$FALMN(T) = \frac{(S_{11}(T) + I_1 \cdot m) \cdot (S_{22}(T) + I_2 \cdot m)}{S_{12}(T) S_{21}(T)}$$

and $$FALMD(T) = \frac{S_{11}(T) \cdot S_{22}(T)}{(S_{12}(T) + I_1 \cdot m) \cdot (S_{21}(T) + I_2 \cdot m)}; \text{ and}$$

the values of $S_{ij}(T)$ each describe the measured light intensity of that light, which after interaction with the measured medium, reaches the receiver $R_j$ from a light source $L_i$.

4. The turbidity measuring device as claimed in claim 1, wherein:
said evaluation circuit includes an evaluation mode, in which a concentration of turbidity-causing material can be ascertained through the four-beam, alternating light method T(FAL) without contributions from monitor signals, and a second evaluation mode, in which a concentration of turbidity-causing material can be ascertained with the contributions of the monitor signals T(FALMN) and/or T(FALMD and
the second evaluation mode is applicable, when T(FAL) falls beneath a limit value.

5. The turbidity measuring device as claimed in claim 3, wherein:
$0.1 < m/c_{ii} < 10$, preferably $0.2 < m/c_{ii} < 5$, and more preferably $0.4 < m/c_{ii} < 2$;
$c_{ii}$ are coefficients, which in the following Equation are necessary for describing the relationships between the measured signal intensity $S_{ii}(T)$ and the concentration T of turbidity causing material, $$S_{ii}(T) = I_i \cdot c_{ii} \cdot T \cdot e^{-\frac{T \cdot X_{ii}}{\lambda}}; \text{ and}$$

$X_{ii}$ is the path length of the light through the measured medium, T is the concentration of turbidity-causing material and $\lambda$ is the average free path length of the light in the case of a reference concentration.

6. A method for turbidity measurement with a four-beam, alternating light arrangement for registering turbidity of a measured medium, comprising the steps of:
registering a first direct signal $S_{11}(T)$ of a first direct measuring path, from a first light source $L_1$, through a measured medium, to a first receiver $R_1$;
registering a second direct signal $S_{22}(T)$ of a second direct measuring path, from a second light source $L_2$ to a second receiver $R_2$;
registering a first indirect signal $S_{12}(T)$ of a first indirect measuring path, from the first light source $L_1$, through the measured medium, to the second receiver $R_2$;
registering a second indirect signal $S_{21}(T)$ of a second indirect measuring path, from the second light source $L_2$, through the measured medium, to the first receiver $R_1$; and
determining turbidity as a function of a quotient A/B, wherein one of the terms A or B is a function at least of the signals registered via the direct measuring paths, and wherein the respectively other term is a function at least of the signals $S_{ij}(T)$ registered via the indirect measuring paths, wherein:
at least a first monitor signal, which depends on the intensity the first light source, enters into one of the two terms A or B;
the light of the first light source reaches the monitor without interaction with the measured medium; and
the monitor signal is added to at least one of signals registered via the measuring paths and entering into term A or B.

7. The method as claimed in claim 6, wherein:
the first monitor signal $I_1 \cdot m$ and a second monitor signal $I_2 \cdot m$ enter into one of the two terms A or B;
the second monitor signal depends upon the intensity of the second light source;
the light of the second light source reaches a monitor receiver without interaction with the measured medium; and
the second monitor signal is added to the other signal ascertained via one of the measuring paths and entering into term A or B.

8. The method as claimed in claim 6, wherein:
turbidity is determined as a function of a measured variable, which is defined either as FALMN(T) or as FALMD(T), where:

$$FALMN(T) = \frac{(S_{11}(T) + I_1 \cdot m) \cdot (S_{22}(T) + I_2 \cdot m)}{S_{12}(T) S_{21}(T)}$$

and $$FALMD(T) = \frac{S_{11}(T) \cdot S_{22}(T)}{(S_{12}(T) + I_1 \cdot m) \cdot (S_{21}(T) + I_2 \cdot m)}; \text{ and}$$

the values of $S_{ij}(T)$ each describe the measured light intensity of that light, which, after interaction with the measured medium, reaches the receiver $R_j$ from a light source $L_i$.

9. The method as claimed in claim 6, wherein:
concentration of turbidity-causing material in the four-beam, alternating light method T(FAL) is ascertained in a first mode without contributions from monitor signals, and is ascertained in a second mode with contributions of the monitor signals T(FALMN) and/or T(FALMD); and
the second evaluation mode is used, when, according to the first mode, T(FAL) falls beneath a limit value.

10. The method as claimed in claim 5, wherein:
$0.1 < m/c_{ii} < 10$, preferably $0.2 < m/c_{ii} < 5$, more preferably $0.4 < m/c_{ii} < 2.5$;
$c_{ii}$ are coefficients, which, in the following equation, are necessary to describe the relationship between the measured signal intensity $S_{ii}(T)$ and the concentration T of turbidity-causing material, $$S_{ii}(T) = I_i \cdot c_{ii} \cdot T \cdot e^{-\frac{T \cdot X_{ii}}{\lambda}}; \text{ and}$$

$X_{ii}$ is the path length of the light through the measured medium, T is the concentration of turbidity-causing material and $\lambda$ is the average free path length of light in the case of a reference concentration.

* * * * *